United States Patent
Kwetkat

Patent Number: 6,034,271
Date of Patent: Mar. 7, 2000

[54] BETAINE GEMINI SURFACTANTS MADE FROM AMINES

[75] Inventor: Klaus Kwetkat, Lünen, Germany

[73] Assignee: Huels Aktiengesellschaft, Marl, Germany

[21] Appl. No.: 09/101,812

[22] PCT Filed: Jan. 9, 1997

[86] PCT No.: PCT/EP97/00055

§ 371 Date: Aug. 31, 1998

§ 102(e) Date: Aug. 31, 1998

[87] PCT Pub. No.: WO97/31890

PCT Pub. Date: Sep. 4, 1997

[30] Foreign Application Priority Data

Mar. 2, 1996 [DE] Germany .......................... 196 08 117

[51] Int. Cl.[7] ...................... C07C 229/22; C07C 229/24; C07C 229/26; C07C 271/02

[52] U.S. Cl. .......................... 562/565; 562/564; 562/555; 254/356

[58] Field of Search .................... 562/565, 555, 562/564; 254/356

[56] References Cited

FOREIGN PATENT DOCUMENTS

| | | |
|---|---|---|
| 0 623 587 A1 | 11/1994 | European Pat. Off. |
| 0 708 079 A1 | 4/1996 | European Pat. Off. |
| 902 258 | 12/1953 | Germany . |
| 43 09 900 | 2/1996 | Germany . |
| 195 05 368 | 8/1996 | Germany . |
| 08 060 183 | 3/1996 | Japan . |
| 08 081 354 | 3/1996 | Japan . |
| 1 137 491 | 12/1968 | United Kingdom . |
| WO 95/19 953 | 7/1995 | WIPO . |
| WO 95/19955 | 7/1995 | WIPO . |
| WO 95/20 026 | 7/1995 | WIPO . |
| WO 9/19 954 | 4/1996 | WIPO . |
| WO 95/19 951 | 9/1997 | WIPO . |
| WO 93/25 646 | 10/1997 | WIPO . |

OTHER PUBLICATIONS

Langmuir 1991, vol. 7, "Alkanediyl–a,w–bis(Dimethylalkylammonium Bromide) Surfactants. 1. Effect of the Spacer Chain Length on the Critical Micelle Concentration and Micelle Ionization Degree", R. Zana, et al. p. 1072–1075.

Nature, vol. 362, Mar. 1993, "Letters to Nature", R. Zana, et al. "Dependence of Aggregate Morphology on Structure of Dimeric Surfactants" p. 228–230.

Langmuir 1993, vol. 9, E.Alami, et al. "Alkanediyl–a, w–bis (Dimethylalkylammonium Bromide) Surfactants. 3. Behavior at the Air–Water Interface", 1465–1467.

Langmuir 1995, vol. 11, R.Zana, et al. "Micellization of Two Triquaternary Ammonium Surfactants in Aqueous Solution" p. 3694–3698.

*Primary Examiner*—Gary Geist
*Assistant Examiner*—Brian J. Davis
*Attorney, Agent, or Firm*—Oblon, Spivak, McClelland, Maier & Neustadt, P.C.

[57] ABSTRACT

Amphiphilic amphoteric compounds of formula (I)

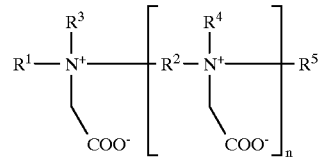

wherein $R^1$, $R^2$, $R^3$, $R^4$, $R^5$, and n are as defined in the disclosure.

15 Claims, No Drawings

BETAINE GEMINI SURFACTANTS MADE FROM AMINES

The invention relates to amphoteric surfactants with at least two hydrophilic and at least two hydrophobic groups (betaine gemini surfactants), which are structured in such a way that complete surfactant units are linked together in each instance.

A large number of anionic, cationic, non-ionic, and hybrid ionic compounds are known as amphiphilic substances. By far most of these substances are composed of a hydrophilic head group and at least one hydrophobic part. For ecological reasons, for example in order to reduce packaging and transport costs, as well as for the purpose of saving natural resources, it is necessary to constantly achieve a greater effect per mass of substance used. Since optimization by means of mixing amphiphilic substances leads only to limited additional results, new amphiphilic substances with a greater degree of effect are necessary. Therefore substances with lower critical micelle formation concentrations and lower surface tensions, in particular, must be found, in order to be able to clearly reduce the amounts of active substance used. In addition, they must be easily obtainable, if possible from easily accessible starting substances.

Preliminary attempts at finding a solution, in the direction of more powerful amphiphilic substances, by doubling part of the structure (hydrophilic head group, hydrophobic group) are already known. For example, cationic surfactant compounds can be obtained by the addition of long-chain alkyl halogenides to permethylated alkylene diamines [R. Zana, M. Benrraou, R. Rueff, Langmuir, 7 (1991) 1072; R. Zana, Y. Talmon, Nature, 362 (1993 228; E. Alami, G. Beinert, P. Marie, R. Zana, Langmuir, 9 (1993) 1465]. Obviously it is possible to improve the performance of surfactant compounds by a suitable linkage of several surfactant units (composed of a hydrophilic head group and a hydrophobic chain) [R. Zana, H. Levy, D. Papoutsi, G. Beinert, Langmuir, 11 (1995) 3694].

Since amphoteric compounds are known to be particularly mild for the skin, it was therefore a particular task to produce amphoteric surfactant compounds which have at least two hydrophilic and two hydrophobic groups, where the amphiphilic compounds have a very high degree of effectiveness, with reference to the amount used, and which furthermore can be produced from raw materials which are easily available on a technical scale, without undesirable by-products. Amphoteric surfactants which can contain two or more hydrophilic groups are described in Offenlegungsschrift DE 43 09 900, but the way in which the structural units are linked there does not result in an increase in performance in comparison with monomer amphoteric surfactants.

The task of increasing performance is achieved, according to the invention, by amphoteric compounds with at least two hydrophilic and at least two hydrophobic groups, which are structured in such a way that complete surfactant units are linked with each other in each instance. Compounds according to Formula (I) are therefore the object of the invention:

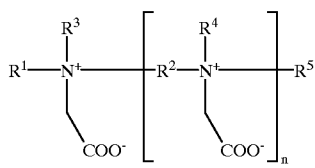

Formula (I)

Here, $R^1$ stands for a saturated or unsaturated, branched or unbranched, cyclic or acyclic hydrocarbon radical with 6 to 22 carbon atoms, $R^2$ stands for a spacer with 2 to 200 atoms, $R^3$ stands for a hydrogen atom or an alkyl radical with 1 to 4 carbon atoms, $R^4$, independent of the other substituents, stands for a saturated or unsaturated, branched or unbranched, cyclic or acyclic hydrocarbon radical with 6 to 22 carbon atoms, and $R^5$ stands for a hydrogen atom or an alkyl radical with 1 to 4 carbon atoms. n can have values from 1 to 100,000, preferably from 1 to 1,000, especially preferably from 1 to 100, and very especially preferably from 1 to 10, where mixtures of different homologues can also occur. Therefore n can also have fractional values, on average.

The compounds according to the invention, according to Formula (I), can occur in mixtures with derivatives which deviate from Formula (I) with regard to the degree of alkylation or protonation.

The spacer $R^2$ is part of a commercially available diamine or a linear, branched, or cyclic polyethylene imine or polyethylene amine (with mean mole masses from 100 to 100,000). Preferred types, however, are characterized by a mean mole mass of less than 10,000. Preferred spacer units contain branched or unbranched hydrocarbons such as —$(CH_2)_2$—, —$(CH_2)_3$—, —$(CH_2)_4$—, —$(CH_2)_5$—, —$(CH_2)_6$—, —$CH_2$—$CH(CH_3)$—$(CH_2)_3$—, furthermore —$(CH_2)_2$—O—$(CH_2)_2$—, —$(CH_2)_2$—O—$(CH_2)_3$—, —$(CH_2)_3$—O—$(CH_2)_3$—, —$(CH_2)_2$—O—$(CH_2)$—O$_2$—$(CH_2)_2$—, —$(CH_2)_3$—O—$(CH_2)$—O$_2$—$(CH_2)_3$—, —$CH_2)_2$—O—$(CH_2)_3$—$(CH_2)_2$—, —$(CH_2)_2$—NH—$(CH_2)_3$—, —$(CH_2)_2$—NH—$(CH_2)_2$—. The spacer contains 0 or 1 to 30 oxygen atoms, preferably 1 to 12 oxygen atoms, and 0 or 1 to 30 nitrogen atoms, preferably 1 to 12 nitrogen atoms.

Mixtures of the aforementioned compounds can also be produced and used.

The amphiphilic surfactant compounds according to this invention are particularly suitable as emulsifiers, demulsifiers, detergents, dispersants, and hydrotropics in industry and household, for example in the fields of metalworking, ore mining, surface finishing, washing and cleaning textiles or hard surfaces, particularly as dishwashing detergents, as well as for washing and cleaning skin and hair, cosmetics, medicine, agrochemicals, and foods processing and preparation. In this connection, they can be combined with any conventional anionic, non-ionic, cationic, and ampholytic surfactant substances.

Without limiting formulations with the surfactants according to the invention to them, the following can be mentioned as examples for non-ionic surfactant substances: fatty acid glycerides, fatty acid polyglycerides, fatty acid esters, alkoxylates of higher alcohols, alkoxylated fatty acid glycerides, polyoxyethylenoxypropylene glycol fatty acid esters, polyoxyethylene sorbitan fatty acid esters, polyoxyethylene castor oil derivatives or derivatives of saturated castor oil, polyoxyethylene lanolin derivatives, polyoxyethylene fatty acid amides, polyoxyethylene alkylamines, derivatives of alkanol amines, alkyl amine oxides, derivatives of protein hydrolizates, mixed hydroxy ethers, alkyl polyglycosides, and alkyl glucamides (e.g. N-methyl alkyl glucamide), as well as non-ionic gemini surfactants, i.e. bridged non-ionic surfactants (as described in WO 95/19951 (polyhydroxyamine compounds), WO 95/19953, WO 95/19954, and WO 95/19955, as well as WO 95/20026).

The following can be mentioned as examples of anionic surfactant substances which can be used for combinations: soaps, ether carboxylic acids and their salts, alkyl sulfonates, α-olefin sulfonates, α-sulfo fatty acid derivatives (including those described in WO 93/25646), sulfonates of higher fatty acid esters, higher alcohol sulfonates (primary and secondary), alcohol ether sulfates, mixed hydroxy ether sulfates, sulfates of alkoxylated carboxylic acid alkanol amides, salts of phosphate esters, taurides, isothionates, linear alkyl benzol sulfonates, bridged alkyl benzol sulfonates (such as DOWFAX types from the Dow company), alkyl aryl sulfonates, sulfates of polyoxyethylene fatty acid amides and derivatives of acylamino acids, alkyl ether carboxylic acids, alkyl and dialkyl sulfosuccinates, alkenyl sulfosuccinates, alkyl or alkenyl sarcosinates, and sulfated glycerin alkyl ethers and gemini surfactants as described in the German patent application 195 05 368.0.

The following can be mentioned as examples of common cationic surfactant substances which can be used for combinations: alkyl trimethyl ammonium salts, dialkyl dimethyl ammonium salts, alkyl dimethyl benzyl ammonium salts, alkyl pyridine salts, quaternated fatty acid esters of alkanol amines, alkyl isoquinolinium salts, benzethonium chlorides and cationic acyl amino acid derivatives.

The following can be mentioned as examples of ampholytes and betaines which can be used for combinations: carbobetaines, such as cocinic alkylamido propyl dimethyl betaine, acylamido pentane diethyl betaine, acylamido propane (or ethane) dimethyl (or diethyl) betaine, all with C chain lengths between 10 and 18, sulfobetaines, imidazole derivatives, soybean oil lipids, and lecithin. The aforementioned amine N-oxides can also be present in polymer form, where a ratio of amine to amine N-oxide of 10:1 to 1:1,000,000 is required. The mean mole mass is 500 to 1,000,000, especially preferably, however, 5,000 to 100,000.

Conventional additives can also be added to the surfactant compounds according to the invention. Such additives are specifically selected for a formulation and usually comprise inorganic salts, such as sodium chloride and sulfate, or also water-soluble calcium and/or magnesium salts, as well as builders, hydrotropics, UV absorbers, plasticizers, chelate-forming agents, viscosity modifiers, enzymes, soil release polymers, bleaches, bleach activators, antiredeposition additives, polymer dispersants, optical brighteners, additives for foam regulation, and fragrances.

The aforementioned compounds according to the invention can be produced according to known methods. Without limiting production to this, a reaction of diamines, oligoamines, or polyamines with aldehydes with a C chain length of 6 to 22 will be mentioned here. In this connection, in the simplest case, an alkyl diimine forms first, and then in the subsequent step, it is reduced with hydrogen, in the presence of a transition metal catalyst, and in the last step, it is carboxymethylated with chloracetic acid or its alkali salt, particularly sodium salt. In this manner, it is possible to ensure that the surfactant units are formed in rather selective manner.

Carboxymethylation is carried out at a temperature of 120 to 160° C., preferably at a temperature of 115 to 145°

C. The reaction time which is required to lower the content of monochloracetic acid and dichloracetic acid to <10 pm is 1 to 10 hours, depending on the reaction temperature. Preferably, the reaction is carried out in two steps.

The resulting products are characterized, in comparison with their conventional equivalents, by significantly lower critical micelle formation concentrations, as well as significantly lower surface tensions of the aqueous solutions of the surfactants according to the invention, as well as significantly lower surface tensions between the said aqueous solutions and various oils, such as paraffin oil, but also thyme oil or various triglycerides. Furthermore, the surfactants according to the invention demonstrate extraordinary mildness and gentleness to the skin.

I claim:

1. Amphiphilic amphoteric compound of Formula (I)

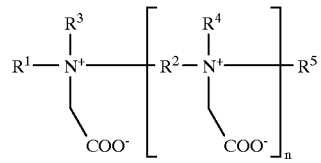

in which $R^1$ stands for a saturated or unsaturated, branched or unbranched, cyclic or acyclic hydrocarbon radical with 6 to 22 carbon atoms, $R^2$ stands for a spacer with 2 to 200 atoms, $R^3$ stands for a hydrogen atom or an alkyl radical with 1 to 4 carbon atoms, $R^4$ stands for a saturated or unsaturated, branched or unbranched, cyclic or acyclic hydrocarbon radical with 6 to 22 carbon atoms, $R^5$ stands for a hydrogen atom or an alkyl radical with 1 to 4 carbon atoms, and n stands for a number from 1 to 100,000, and their mixtures.

2. Amphiphilic amphoteric compound according to claim 1, wherein
n in Formula (I) assumes a value from 1 to 1,000.

3. Amphiphilic amphoteric compound according to claim 1, wherein
the spacer $R^2$ contains a branched or unbranched hydrocarbon chain.

4. Amphiphilic amphoteric compound according to claim 1, wherein
the spacer $R^2$ contains 1 to 30 oxygen atoms.

5. Amphiphilic amphoteric compound according to claim 1, wherein
the spacer $R^2$ contains 1 to 30 nitrogen atoms.

6. Method for the production of the amphiphilic amphoteric compound according claim 1, comprising
reacting a diamine, oligoamine, or polyamine with an aldehyde with a C chain length of 6 to 22 to form a reaction product, and then reducing the reaction product with hydrogen and carboxymethylating with chloracetic acid or its sodium salt.

7. A process comprising emulsifying or demulsifying with the amphiphilic compound according to claim 1.

8. A metal working process, an ore mining process or a surface finishing process comprising emulsifying or demulsifying with the amphiphilic compound according to claim 1.

9. A process comprising dispersing agrochemicals with the amphiphilic compound according to claim 1.

10. A process comprising washing and cleaning textiles with the amphiphilic compound according to claim 1.

11. A process comprising cleaning hard surfaces with the amphiphilic compound according to claim 1.

12. A process comprising washing skin and hair with the amphiphilic compound according to claim 1.

13. Amphiphilic amphoteric compound according to claim 4, wherein the spacer $R^2$ contains 1 to 12 oxygen atoms.

14. Amphiphilic amphoteric compound according to claim 5, wherein the spacer $R^2$ contains 1 to 12 nitrogen atoms.

15. Process of claim 11, wherein the hard surfaces are dishes.

* * * * *